United States Patent
Donskoy et al.

(10) Patent No.: US 6,415,666 B1
(45) Date of Patent: Jul. 9, 2002

(54) METHOD AND APPARATUS FOR ACOUSTIC DETECTION OF MINES AND OTHER BURIED MAN-MADE OBJECTS

(75) Inventors: Dimitri M. Donskoy; Alexander M. Sutin, both of Hoboken, NJ (US)

(73) Assignee: Stevens Institute of Technology

(*) Notice: Subject to any disclaimer, the term of this patent is extended or adjusted under 35 U.S.C. 154(b) by 0 days.

(21) Appl. No.: 09/462,956

(22) PCT Filed: Jul. 15, 1998

(86) PCT No.: PCT/US98/14443
§ 371 (c)(1),
(2), (4) Date: Mar. 20, 2000

(87) PCT Pub. No.: WO99/04287
PCT Pub. Date: Jan. 28, 1999

Related U.S. Application Data

(60) Provisional application No. 60/062,576, filed on Oct. 7, 1997.

(51) Int. Cl.[7] ............................. G01N 29/00; G01S 15/00
(52) U.S. Cl. ........................................... 73/627; 367/87
(58) Field of Search ........................ 73/627, 602, 599, 73/596; 367/87

(56) References Cited

U.S. PATENT DOCUMENTS

| | | | | | |
|---|---|---|---|---|---|
| 3,292,143 | A | * | 12/1966 | Russell | 340/15.5 |
| 3,705,381 | A | * | 12/1972 | Pipkin | 340/3 R |
| 3,786,405 | A | * | 1/1974 | Chramiec et al. | 340/3 |
| 4,308,599 | A | * | 12/1981 | Thiele | 367/92 |
| 4,439,845 | A | * | 3/1984 | Geohegan, Jr. et al. | 367/87 |
| 4,922,467 | A | * | 5/1990 | Caufield | 367/87 |
| 5,357,063 | A | * | 10/1994 | House et al. | 181/108 |
| 5,563,848 | A | * | 10/1996 | Rogers et al. | 367/99 |
| 5,736,642 | A | * | 4/1998 | Yost et al. | 73/602 |
| 5,819,859 | A | * | 10/1998 | Stump et al. | 175/26 |
| 5,974,881 | A | * | 11/1999 | Donsky et al. | 73/579 |

* cited by examiner

Primary Examiner—Richard A. Moller
(74) Attorney, Agent, or Firm—Adams & Wilks

(57) ABSTRACT

In order to detect buried compliant objects such as land mines and pipes, an acoustic signal is directed into the ground to excite vibration of a buried compliant object. A probing signal is also directed into the ground toward the vibrating object, and the probing signal is modulated and reflected by the vibrating object. The modulated, reflected probing signal is processed to determine therefrom the presence of the buried compliant object.

23 Claims, 5 Drawing Sheets

METHOD AND APPARATUS FOR ACOUSTIC DETECTION OF MINES AND OTHER BURIED MAN-MADE OBJECTS

This application claims benefit of Provisional Application Serial No. 60/062,576 filed Oct. 7, 1997.

BACKGROUND OF THE INVENTION

1. Field of the Invention

The present invention generally relates to a method and apparatus for acoustic detection of buried man-made objects, and more particularly to a method and apparatus which emits an acoustic signal comprising one or more frequencies and measures vibrations of the ground/sediment surface to detect buried objects such as mines. The present invention also relates to a method and apparatus which emits an electromagnetic RF probing signal and sound or vibration signal (modulating signal), detects the reflected electromagnetic signal from the buried object, and processes the received signal, identifying the modulation caused by vibration.

2. Related Art

The oldest and probably the most common method of locating land mines involves prodding the ground with a stick or other implement to locate a nine. Presently, metal detectors are used to detect mines by measuring the disturbance of an emitted electromagnetic field caused by the presence of metallic objects in the ground. For ferromagnetic objects, magnetometers are employed. These sensors measure the disturbance of the earth's natural electromagnetic field. Both types of detectors cannot differentiate a mine from metallic debris, leading to 100–1000 false alarms for each real mine. In addition, most of the modern antipersonnel mines are made of plastic with very few or no metal parts, making them undetectable by metal detectors.

New methods for detecting mines involve ground-penetrating radar, infrared imaging, X-ray backscatter technique, and thermal neutron activation, Gros and Bruschini, "Sensor technologies for detection of antipersonnel mines" A survey of current research and system developments, International Symposium on Measurement and Control in Robotics (ISMCR'96), Brussels, May, 1996. These methods (except the thermal neutron activation) rely on imaging and cannot differentiate a mine from rocks or other debris. The drawbacks of the thermal neutron activation technique, apart from system complexity, are the limited depth of penetration and the potential danger to the operator due to the neutron source.

There are a number of acoustic methods of detecting buried objects such as mines. One such method is set forth by Don and Rogers, "Using acoustic impulses to identify a buried non metallic object" Journal of Acoustical Society of America, 95(5), Part 2, 1994, which describes measuring acoustic reflection from an object and comparing it to a measurement taken at a microphone positioned over a homogeneous matrix. Likewise, the following patents provide the examples of the acoustic detection methods:

House. et al., U.S. Pat. No. 5,357,063, discloses a method and apparatus for acoustic energy identification of objects buried in soil. This method identifies a buried object by viewing the images of the acoustic energy reflected from the soil and, therefore, is unable to differentiate a mine from debris with the similar acoustic reflectivity.

Rogers. et al., U.S. Pat. No. 5,563,848, compares a reflected signal with a reference signal reflected from the ground where presumably no buried objects are located The differences between these two signals indicates the presence of an object. The drawback of this method is that any variations in the physical properties of the ground (density, porosity, moisture content, etc.) as well as the presence of non-target objects (rocks, tree and grass roots, debris, etc.) will create a difference from the reference signal and, consequently, lead to a high rate of the false alarms.

Caulfield, U.S. Pat. No. 4,922,467, discloses an acoustic detection method based on comparison of the measured "signature" of the object with the predetermined and stored reference "signatures." The signature is derived from the properties of the object such as acoustic impedance, absorption, velocity and porosity. This method is intended to identify the substance inside an enclosure and may work well for detecting and identifying substances in enclosures with known acoustical properties such as a suitcase, mail package, etc. However, when the enclosure is the earth, this method may not work at all because the acoustical properties of the earth may vary in wide ranges which cannot be predicted. Therefore, these unknown variations in the acoustical properties of the "enclosure" (earth) will interfere with the determination of the properties of the buried object.

Geohegan. Jr., et al., U.S. Pat. No. 4,439,485, discloses a sonar system for identification of certain resonant body targets such as mines. The system radiates two acoustic signals of different frequencies $F_1$ and $F_2$ which are transmitted toward the target and the acoustic returns are separated into the component frequencies, detected, and thereafter subtracted from one another. A signal above a threshold value indicates a resonant body target. The received signals have the same $F_1$ and $F_2$ frequencies as the radiated signals. The frequencies $F_1$ and $F_2$ must be within the resonance frequency of the expected target. A processing algorithm subtracts envelopes of received signals with the frequencies $F_1$ and $F_2$ looking at the time-variation of the resulting signal due to a resonance "ringing" effect from resonating target.

Pipkin U.S. Pat. No. 3,705,381, discloses a resonant target sonar system for detection and classification of underwater targets. The system broadcasts two signals: one is a high frequency signal, and the other one is a low frequency signal with the frequency "substantially similar to the resonant frequency of the target." This patent searches resonance targets and requires prior knowledge of their resonance frequencies. Processing of the signals consists of subtraction (in time domain) of two high frequency signals reflected from the target: one is reflected from the target during the broadcasting resonant low frequency signal, and another one without the resonant signal.

Au. et al., U.S. Pat. No. 3,786,405, discloses a communication system which utilizes a well known parametric sonar, first published in 1968 by Westervelt, and is aimed to generate narrow beam low frequency sound signals. It radiates two high frequency highly directional signals (primary signals) into a nonlinear medium such as water. Nonlinear interaction of the primary signals within the water column generates narrow beam secondary radiation at a difference frequency. This phenomenon has nothing to do with a target and takes place in the water column. Once the secondary signal is formed, it can be used for various applications as any other directly radiated signal.

Bealor. et al., U.S. Pat. No. 3,757,287, discloses a sea bottom classifying sonar with several transducers. It broadcasts and receives acoustical signals with the same frequency as ordinary sonar.

Moore, U.S. Pat. No. 3,603,919, discloses a radar or sonar system including a continuous spectrum of electromagnetic or compressional wave energy transmitted to define a wide band of frequencies.

None of these previous efforts, taken either alone or in combination, teach or suggest all of the elements, nor the benefits and utility of the present invention.

OBJECTS AND SUMMARY OF THE INVENTION

It is a primary object of the present invention to provide a method and apparatus for the detection of metal and non-metal man-made objects buried in the ground or sea sediments.

It is another object of the invention to provide a method and apparatus to identify specific buried objects.

It is another object of the present invention to provide a method and apparatus to detect unexploded ordinances, (or mines, shells, etc.), in various forms, buried in earth or in sediment under water.

It is an additional object of the present invention to provide a method and apparatus for identifying compliant items buried in earth or in sediment under water.

It is a further object of the present invention to provide a method and apparatus for detecting mines by virtue of vibrating the compliant casings of the mines.

It is still a further object of the present invention to provide a method and apparatus for causing a casing of a land mine to vibrate, and then to detect such vibration to locate a mine.

It is even a further object of the present invention to provide a low frequency signal to penetrate the ground and excite vibrations of a buried object.

It is an additional object of the present invention to provide a method and apparatus for locating buried mines which employs a sensing signal comprising two or more frequencies.

It is yet an additional object of the present invention to provide a method and apparatus which measures vibrations caused by compliant articles.

It is an additional object of the present invention to provide a method and apparatus for detecting buried objects which delivers a seismic probe signal to the ground.

It is even an additional object of the present invention to provide a method and apparatus for detecting buried objects which includes a sensor placed on or above the ground for measuring vibration caused by a compliant article.

These and other objects are achieved by the method and apparatus of the present invention which employs low frequency waves containing one or more frequencies for penetrating into ground, water, or sediments and exciting vibrations of a buried object. When these sound waves encounter an acoustically compliant object such as a mine, the sound waves vibrate the compliant object, which, in turn, vibrates against the boundaries of the surrounding medium, such as the ground or sediment This creates a non-linear distortion of the probing signal, including the generation of harmonics and acoustic waves with combination frequencies (nonlinear signals). These nonlinear vibrating signals are received from the surface by means of a sensor. The amplitude of the measured nonlinear signals indicates the presence of an acoustically compliant object such as a mine. The acoustically compliant object can be identified when the probe signal includes more than one frequency.

In another embodiment, the present invention employs the effect of modulation of a probing RF signal by the vibration of a buried object. The invention employs an RF probing signal capable of penetrating underground and an acoustic signal. These signals are transmitted toward a target. The acoustic signal excites vibration of the buried object. Such vibration is much larger for acoustically compliant objects such as mines, unexploded ordinance, pipes and other shell-type object, as compared with much less compliant solid objects (rocks, tree roots, etc.).

The RF probing signal reaches the object, reflects back and is then received by a receiving antenna. Vibration of the compliant objects causes modulation of the reflected RF signal. The presence of this modulation serves as an object discrimination characteristic, since less compliant non-target objects (rocks, tree roots, etc.) reflect the RF signal without the modulation.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

Figure 1:
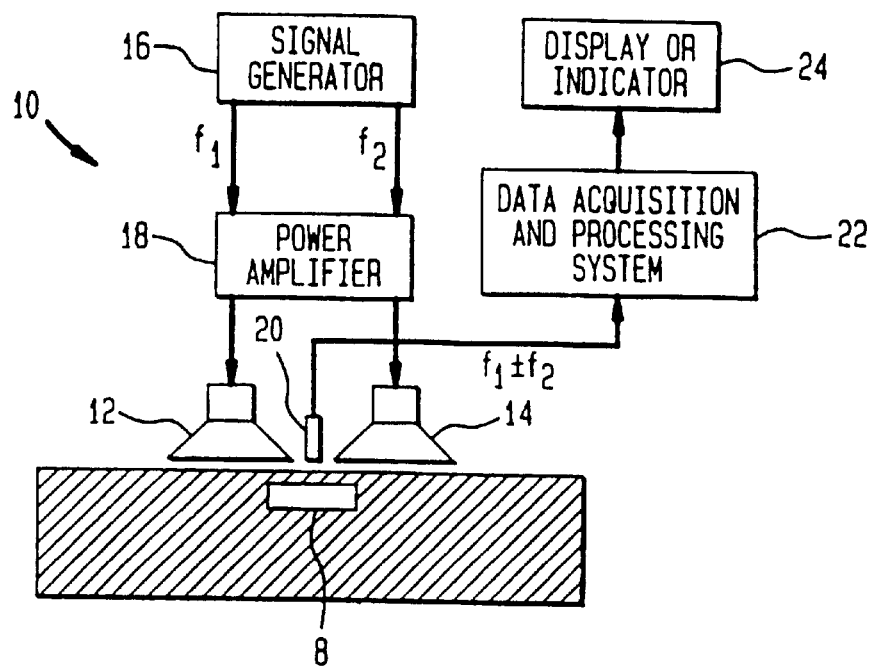
FIG. 1 is a schematic diagram of an embodiment of the apparatus of the present invention.
Figure 2:
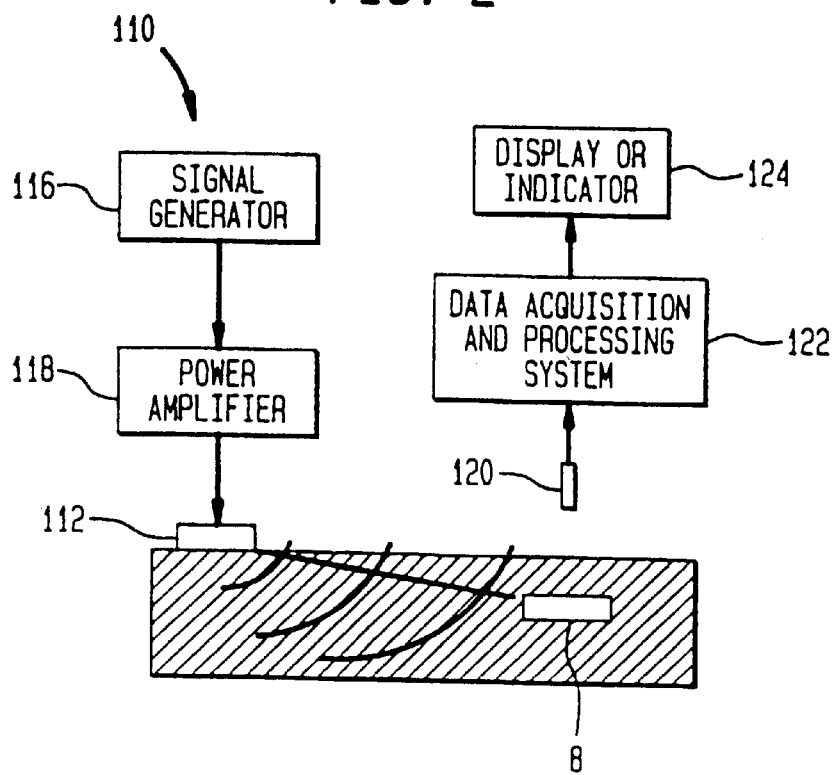
FIG. 2 is a schematic diagram of another embodiment of the apparatus of the present invention.

The present invention relates to a method and apparatus for the acoustic detection of buried, man-made objects such as mines. A schematic of one embodiment of the apparatus of the present invention is shown in the FIG. 1. The detecting apparatus is generally indicated at 10. A probe sound signal is emitted by one or more sound sources 12 and 14 suspended above the ground. The probe signal can be created with a signal generator 16 and a power amplifier 18. Each of the one or more sound sources 12 and 14 emits a signal, preferably a finite duration (burst) sinusoidal signal, with a given frequencies such as frequencies $f_1$ and $f_2$. The sound sources could be electric powered (such as loudspeakers, etc.) or air powered (air horns). In the latter case the signal generator and the power amplifier can be substituted with a compressed gas source. In the embodiment of the invention shown in the FIG. 2, for example, wherein the apparatus is generally indicated at 110, the probe signal is emitted by an acoustic (seismic) source (sources) 112 located directly on the ground.

The probe signal penetrates the ground and interacts with a compliant buried object 8 such as a mine. A compliant object is an object whose compliance in the specified frequency range is different from the compliance of the surrounding media Mines have shells which are generally compliant. Acoustic energy is used as a probe for a compliant object. As a result of the nonlinear interaction at the object-medium interface, a signal with combination frequencies $f_1 \pm f_2$ is generated. This signal, in turn, causes vibration of the surface of the ground above the buried object. This vibration is received with a sensor 20 or 120 and processed by a processor 22 or 122 to extract the signal with the combination frequencies $f_1 \pm f_2$. This signal can then be displayed by display 24 or 124. The receiving sensor 20 or 120 could be an accelerometer (placed on the ground-contact sensor) or a microphone or ultrasonic (or laser) vibrometer suspended above the ground. Additionally, it should be pointed out that such sensing can be performed remotely. A signal with the combination frequencies $f_1 \pm f_2$ exceeding a predetermined threshold level, which is set during calibration of the apparatus, indicates the presence of a compliant object 8. While the probe signal is in one frequency range, the received signal, or vibration signal can be in a different frequency range.

The method of the present invention can be further enhanced by implementing the measurement of the nonlinear frequency response of the object. The nonlinear frequency response can be obtained by sweeping one or both excitation frequencies $f_1$ and $f_2$ within the range $\Delta f$, or by radiating a multi-frequency signal in the same range $\Delta f$. Observation of the difference frequency $f_1 - f_2$, while sweeping, for example $f_1$ will produce a nonlinear frequency response of the object in the frequency range $\Delta f$. It was observed experimentally, that a compliant object produces a resonance-like response, while non-compliant objects return practically no response at all. Therefore, the observation of the resonance-like nonlinear response can be used, in addition to the combination frequency observation, to further increase the detection probability of the method of the present invention. It was also experimentally observed that the nonlinear resonance frequency varies for various objects. This, therefore, can be additionally utilized for identification of a particular object. Accordingly, a reference nonlinear frequency response can be used for object identification. There is no need for a reference signal for object detection.

Figure 3:
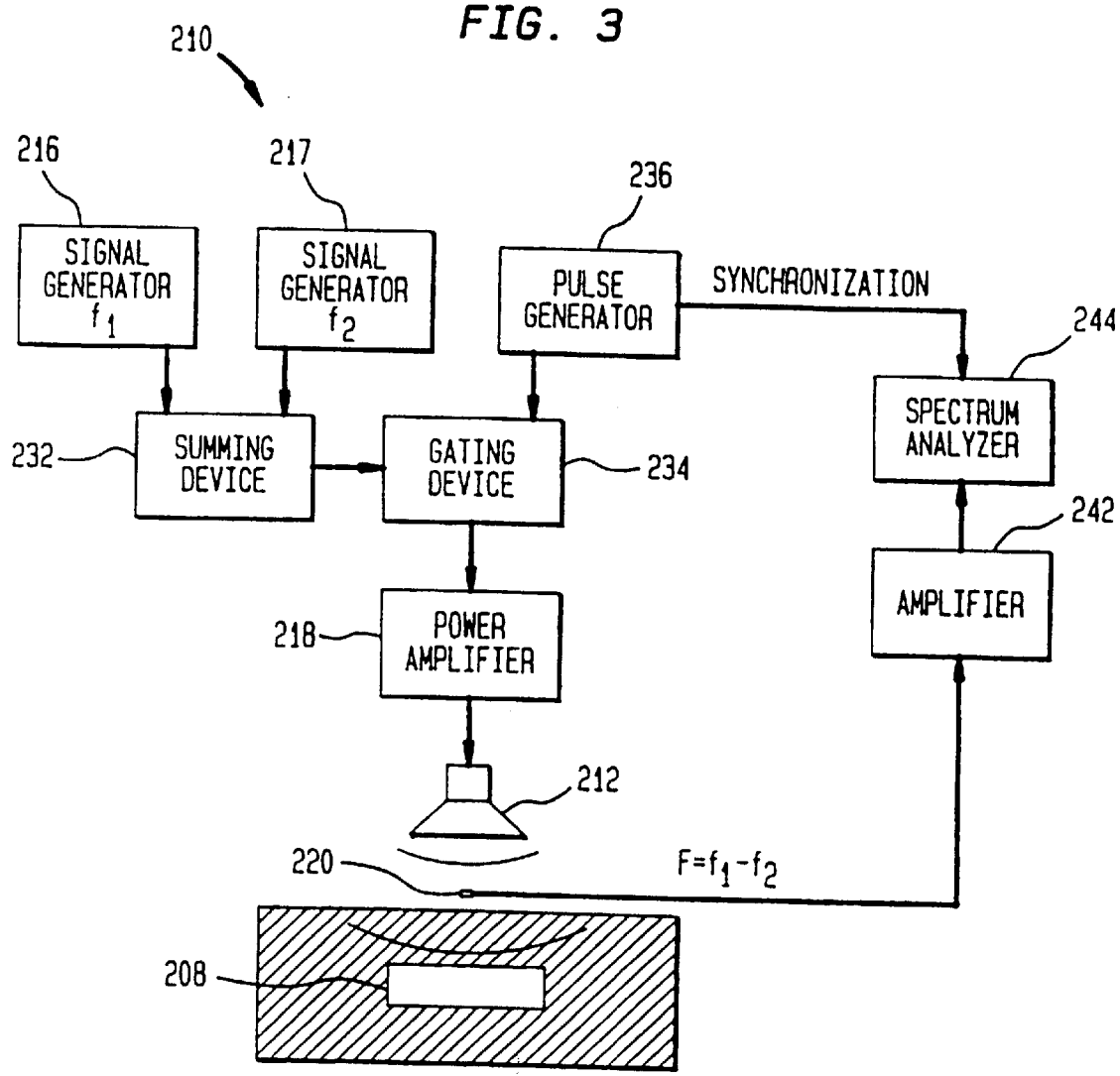
FIG. 3 is a schematic diagram of an experimental apparatus used for conducting experiments according to the present invention.

The experimental setup 210, shown in the FIG. 3, employs two signal generators 216 and 217 respectively, supplying sinusoidal signals with the frequencies $f_1$ and $f_2$, respectively, the summing and gating devices 232 and 234 forming a probe bi-harmonic burst signal. The duration of the burst is controlled with a pulse generator 236. After amplification by means of power amplifier 218, the probe signal radiates from a loudspeaker 212 suspended above the ground where the object 8 is buried. The vibration of the ground surface is picked up with an accelerometer 220 and processed with a spectrum analyzer 244 after the signal is fed through an amp 242.

Figure 4A:
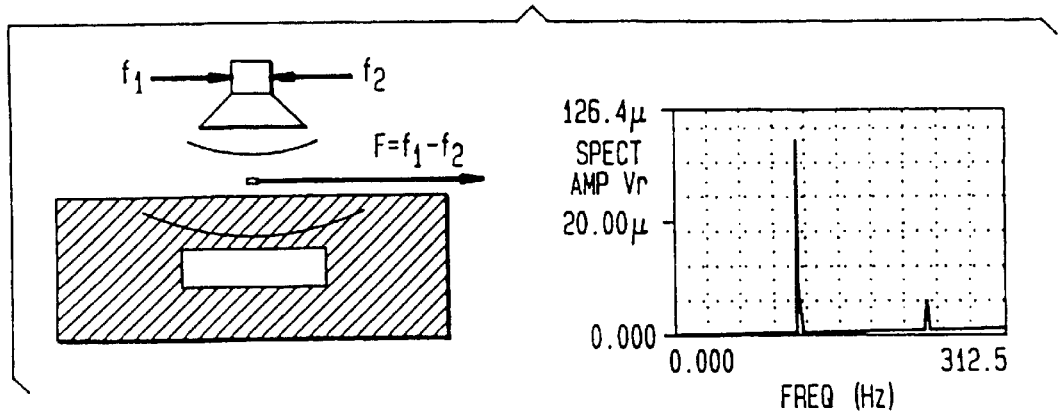
FIGS. 4a, 4b, and 4c show schematic diagrams and a corresponding graph of the spectrum level of the difference frequency signal.
Figure 4B:
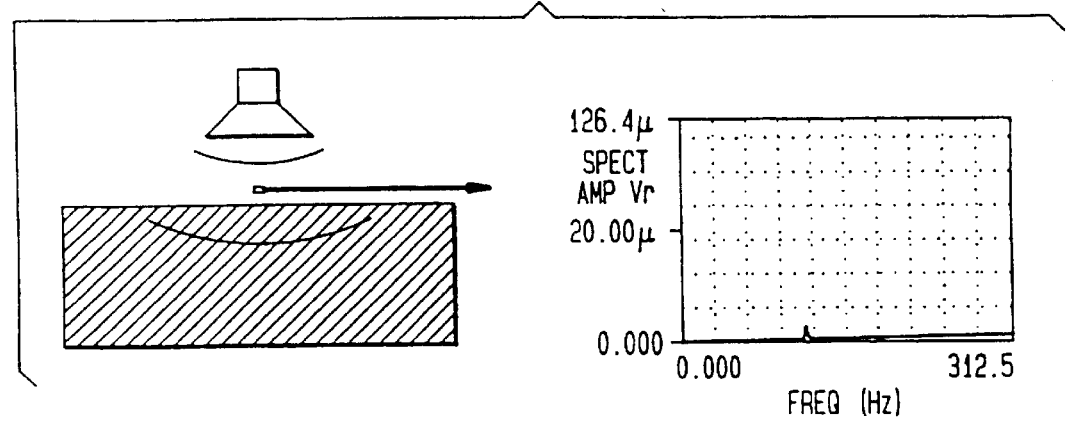
Figure 4C:
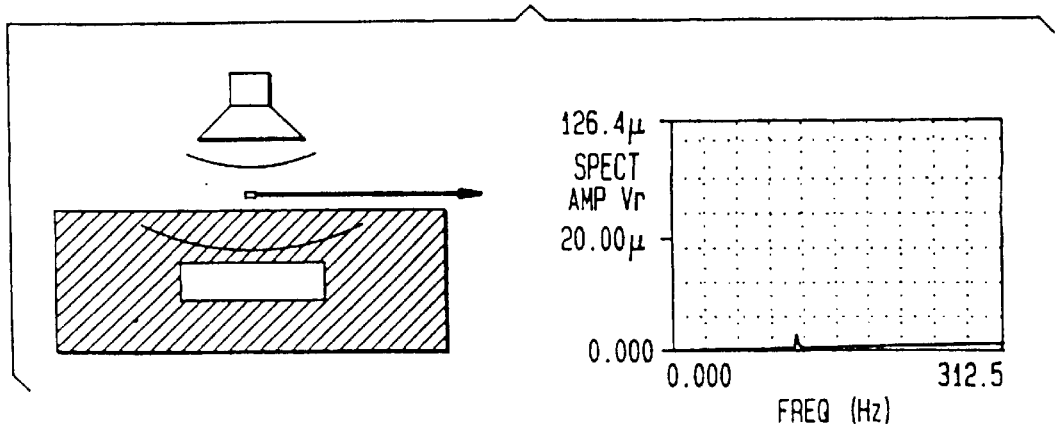

FIG. 4 shows examples of the spectral component of the difference frequency, $f_1 - f_2$, received from a compliant plastic container (FIG. 4a), a background level (no object is buried) (FIG. 4b), and solid steel disk (FIG. 4c). As can be seen, the level of the signal from the compliant plastic container is 16 times greater than the signal from the solid non-compliant steel disk, as well as the background signal.

Figure 5A:
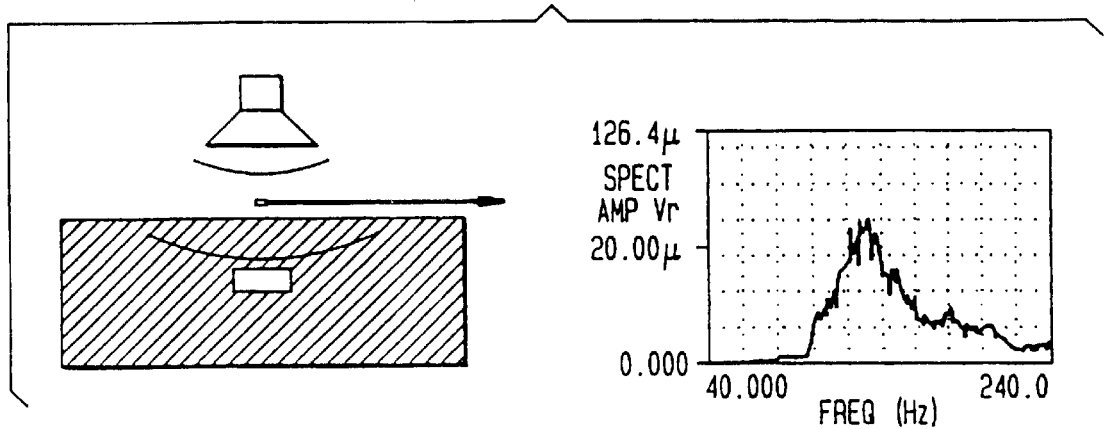
FIGS. 5a, 5b and 5c show schematic diagrams and a corresponding graph of nonlinear frequency responses.
Figure 5B:
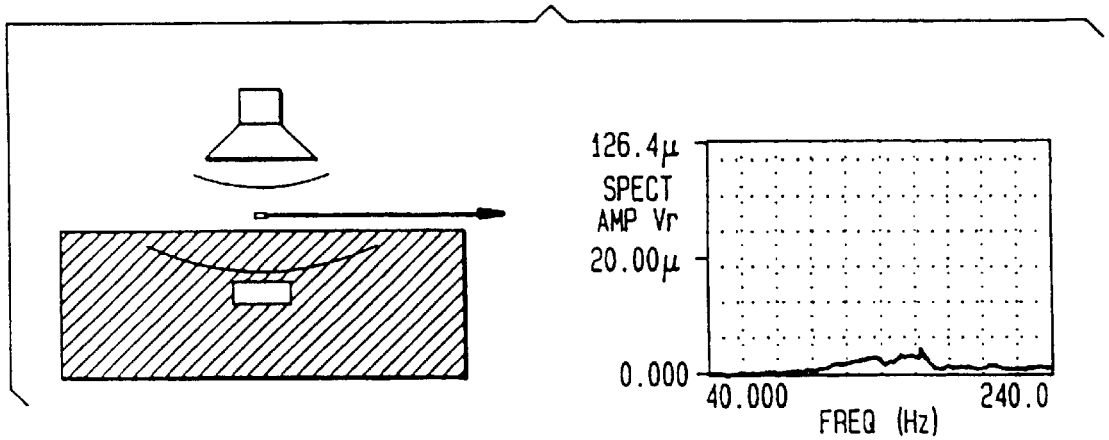
Figure 5C:
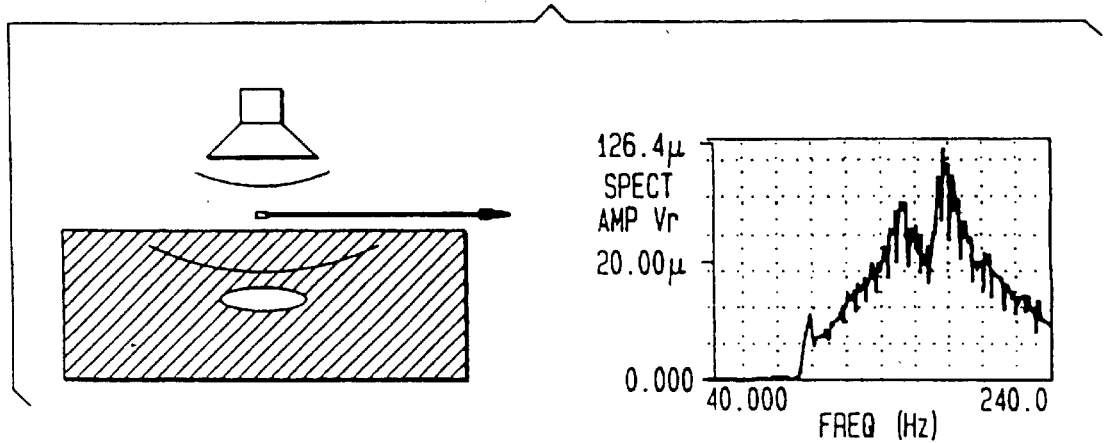

FIG. 5 depicts examples of the nonlinear frequency responses from two different compliant objects, namely, a four and one half inch plastic cylindrical container (FIG. 5a) a four inch steel disk (FIG. 5b) and a four inch solid steel container (FIG. 5c). These spectra show that the response from the compliant containers have nonlinear resonances while the non-compliant steel object produces no such resonances.

Figure 6:
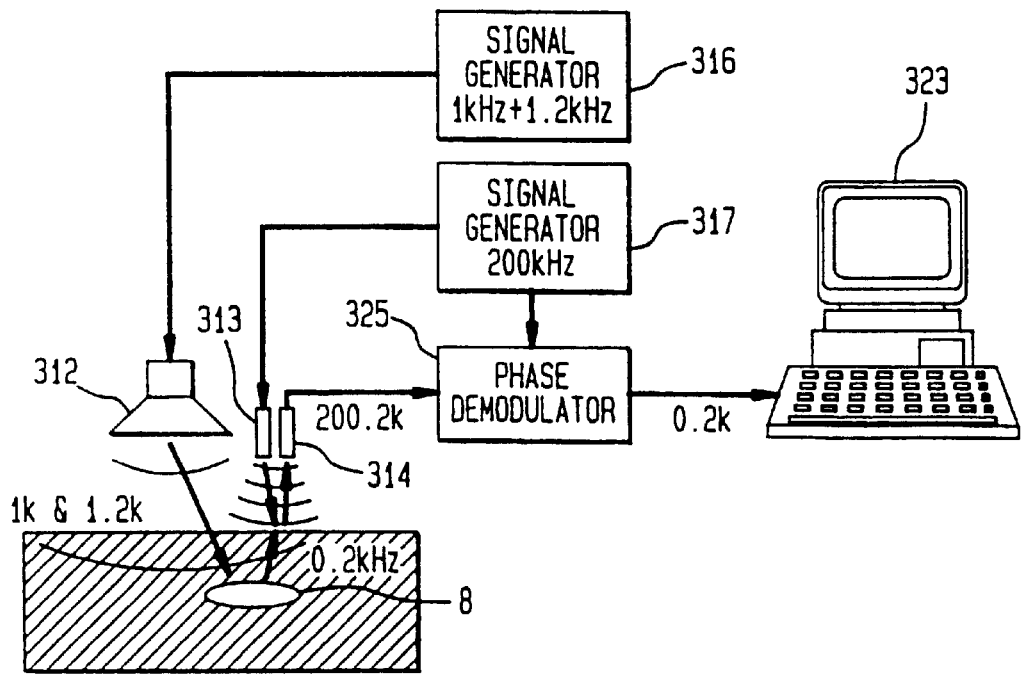
FIG. 6 is a schematic diagram of another embodiment of the apparatus of the present invention.

FIG. 6 shows another embodiment of the present invention wherein two signal generators 316 feeds source 312 to create a probe signal to vibrate compliant object 8. The source 313 emits a high frequency ultrasonic signal to pick up vibration. The vibrations are sensed by sensor 314 and fed to signal acquisition 325 such as an Ultrasonic Vibrometer, and then fed to signal processing 323 wherein the signal can be processed and displayed.

The present invention is based on the effect of nonlinear interactions between the compliant housing of the buried object and the surrounding media Preferably, low frequency (below 5000 Hz) air/water-borne or solid-borne sound waves (the probe signal) containing two or more frequencies are utilized. This probe signal penetrates into the ground/sediments and excites vibrations of the buried object. For acoustically compliant objects such as mines (as opposed to stones, solid metal objects, bricks, etc., which are much less compliant) these vibrations lead to "bouncing" of the object boundaries against the surrounding medium. The acoustical manifestation of this phenomenon is the nonlinear distortion of the probing signal including the generation of harmonics and acoustic waves with the combination frequencies (nonlinear signals). These nonlinear vibrating signals are picked up from the surface of the ground/sediments with a sensor. The amplitude of the measured nonlinear signals indicates the presence of an acoustically compliant object. This allows for the detection of non-metallic objects (e.g. plastic mines and pipes), with non-sensitivity to less-compliant objects such as rocks, solid metal objects, tree roots, etc.

The method of the present invention can be practiced in a portable or semi-stationary mode. Basically, the method includes producing an acoustic signal such as a sound or seismic acoustic signal which is directed either through water, air, or sediments to the ground and then into the ground where a mine or other compliant object may be buried. The acoustic signal can be emitted by means of loudspeakers, air horns, or a seismic source or other means known in the art. The signal may include more than one frequency component and may include one or more sources for emitting the signal. The signal travels into the ground where it encounters a compliant object and causes the compliant object to vibrate. This vibration impacts the surrounding medium and causes same to vibrate, creating a nonlinear distortion and generating harmonics and acoustic waves. These vibration signals are received by a sensor on or above the surface of the ground or other medium. These signals are fed through a processor to analyze same for determination of the existence of a compliant object.

Figure 7:
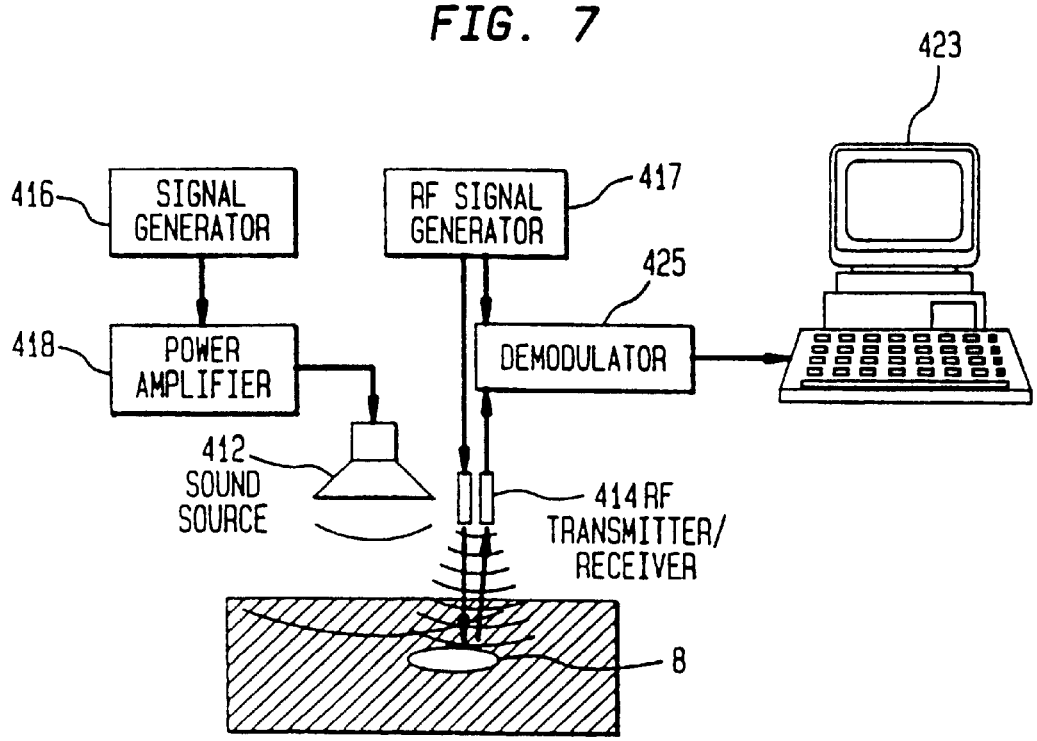
FIG. 7 is a schematic diagram of another embodiment of the apparatus of the present invention.

Referring now to FIG. 7, another embodiment of the present invention is shown. This embodiment of the invention employs a signal generator 416, a power amplifier for amplifying the signal and a source 412 for emitting the acoustic signal. The acoustic signal vibrates a compliant object 8. An RF signal generator 417 is employed to create a ground penetrating RF probing signal. The RF probing signal is reflected back to a sensor 414 and then fed into a demodulator 425 and then to a signal processor 423 such as a computer. The vibration of the compliant object caused by the acoustic signal modulates the reflected RF signal to allow this embodiment of the invention to serve as an object discriminator. The RF signal can be a burst sinusoidal signal and may be synchronously admitted with a RF transmitter also suspended above the ground. Both the acoustic and the RF signals penetrate into the ground. The acoustic signal excites vibration of the buried mechanically compliant target This vibration causes a phase or frequency modulation of the RF signal reflected from the vibrated target. This modulated signal is then received by the receiver, demodulated and analyzed to detect the presence of the modulation frequencies. The presence of modulation frequencies indicates the presence of the compliant target such as a mine.

There could be various modes of operation utilizing the radio-acoustic modulation effect. One mode may involve a CW air or solid borne signal causing the Doppler shift of a reflected RF probing signal. Another mode may employ a more complex acoustic signal, such as a dual frequency (frequencies $f_1$ and $f_2$) signal. This signal, in addition to vibration excitation of the target with the same frequencies $f_1$ and $f_2$, causes a nonlinear transformation of target vibration into the combination frequencies $f_1 \pm f_2$ and $f_1 - f_2$ due to the nonlinear interaction of the vibrating target interface and the surrounding soil. These frequencies will also produce the modulation of the RF signal, further enhancing the discrimination capabilities of the invented detection technique.

The processing unit of the device of this invention incorporates the means or steps of demodulation of the received signal by multiplying the received RF signal by a reference signal corresponding to the initially radiated RF signal, low-pass filtering, and post-processing such as the spectral analysis to identify the presence of the modulating frequencies.

Among the advantages of the proposed technique are: the capability to detect non-metallic objects (e.g. plastic and wooden mines and pipes); non-sensitivity to less-compliant objects such as rocks, solid metal objects, tree roots, etc.; identification capabilities, since the measured response depends on structural properties of the object; and simplicity and low cost.

The invented technique can be utilized as a stand alone device or combined with existing target detection devices such as ground penetrating RADAR In this case the GPR's, RF transmitting/receiving equipment can be combined to implement invented technique. This can be a complimentary mode of operation of GPR, greatly enhancing its discrimination capability.

Having thus described the invention in detail, it is to be understood that the foregoing description is not intended to limit the spirit and scope thereof. What is desired to be protected by Letters Patent is set forth in the appended claims.

What is claimed is:

1. An apparatus for detecting compliant buried objects comprising:
   signal generating means for generating an acoustic signal having first and second frequencies for vibrating a compliant buried object;
   RF signal generating means for generating an RF signal which is directed, separately from the acoustic signal, toward the vibrating buried object so that the vibrating buried object modulates the RF signal;
   receiving means for receiving the RF signal after the RF signal is modulated by the vibrating buried object; and
   processing means for processing the signal received by the receiving means.

2. The apparatus of claim 1; wherein the signal generating means includes power amplifying means for amplifying the acoustic signal.

3. The apparatus of claim 2; wherein the signal generating means generates a dual frequency acoustic signal.

4. The apparatus of claim 3 further comprising demodulation means for demodulating the received signal.

5. The apparatus of claim 4 wherein the RF signal generating means generates a ground penetrating RADAR signal.

6. A method of locating a buried compliant object, comprising the steps of:
   producing an acoustic signal;
   directing the acoustic signal at a buried compliant object to vibrate the object;
   producing a second signal;
   directing the second signal at the vibrating buried compliant object to cause the second signal to be modulated by the vibrating object; and
   processing the modulated second signal to determine the presence of the buried compliant object.

7. The method of claim 6; wherein the second signal comprises an RF signal.

8. The method of claim 7; wherein the RF signal comprises a ground penetrating RADAR signal.

9. The method of claim 8 further comprising the step of demodulating the modulated second signal.

10. An apparatus for detecting buried compliant objects comprising: a first signal generator for generating an acoustic signal to excite vibration of a buried compliant object; a second signal generator for generating a probing signal which is directed separately from the acoustic signal toward and modulated by the vibrating buried compliant object; a receiver disposed to receive the modulated probing signal; and a processor connected to the receiver for processing the modulated probing signal to determine therefrom the presence of the buried compliant object.

11. An apparatus according to claim 10; further including a sound source connected to the first signal generator for directing the acoustic signal toward the buried compliant object.

12. An apparatus according to claim 10; further including a demodulator connected to the receiver for demodulating the modulated probing signal and outputting a demodulated probing signal to the processor.

13. An apparatus according to claim 10; wherein the first signal generator generates a dual frequency acoustic signal.

14. An apparatus according to claim 13; wherein the second signal generator generates an RF probing signal.

15. An apparatus according to claim 10; wherein the second signal generator generates an RF probing signal.

16. An apparatus according to claim 10; wherein the second signal generator generates a ground penetrating RADAR probing signal.

17. An apparatus according to claim 16; wherein the first signal generator generates a dual frequency acoustic signal.

18. A method of detecting buried compliant objects, comprising the steps:
   directing an acoustic signal toward a buried compliant object to excite the object to vibrate;
   directing a probing signal toward the vibrating buried compliant object to cause the probing signal to be modulated and reflected by the vibrating object; and
   processing the modulated, reflected probing signal to determine therefrom the presence of the buried compliant object.

19. A method according to claim 18; wherein the acoustic signal comprises a dual frequency acoustic signal.

20. A method according to claim 19; wherein the probing signal comprises an RF probing signal.

21. A method according to claim 18; wherein the probing signal comprises an RF probing signal.

22. A method according to claim 18; wherein the probing signal comprises a ground penetrating RADAR probing signal.

23. A method according to claim 22; wherein the acoustic signal comprises a dual frequency acoustic signal.

* * * * *